US010441253B2

(12) United States Patent
Gundberg et al.

(10) Patent No.: US 10,441,253 B2
(45) Date of Patent: Oct. 15, 2019

(54) ENDOSCOPIC DEVICE FOR MULTIPLE SAMPLE BIOPSY

(71) Applicant: BioScopeX ApS, Struer (DK)

(72) Inventors: Tomas Gundberg, Viby Sjælland (DK); Ole Kjeldsen, Struer (DK); Henrik Harboe, Copenhagen K (DK)

(73) Assignee: BioScopeX ApS, Struer (DK)

( * ) Notice: Subject to any disclaimer, the term of this patent is extended or adjusted under 35 U.S.C. 154(b) by 436 days.

(21) Appl. No.: 15/031,951

(22) PCT Filed: Oct. 28, 2014

(86) PCT No.: PCT/EP2014/073089
§ 371 (c)(1),
(2) Date: Apr. 25, 2016

(87) PCT Pub. No.: WO2015/063071
PCT Pub. Date: May 7, 2015

(65) Prior Publication Data
US 2016/0262735 A1 Sep. 15, 2016

(30) Foreign Application Priority Data
Oct. 30, 2013 (EP) .................................... 13190858

(51) Int. Cl.
A61B 10/04 (2006.01)
A61B 10/02 (2006.01)
(Continued)

(52) U.S. Cl.
CPC .............. A61B 10/04 (2013.01); A61B 1/018 (2013.01); A61B 10/0266 (2013.01);
(Continued)

(58) Field of Classification Search
CPC .................. A61B 10/04; A61B 10/06
See application file for complete search history.

(56) References Cited

U.S. PATENT DOCUMENTS 5,373,854 A 12/1994 Kolozsi
5,562,102 A 10/1996 Taylor
(Continued)

FOREIGN PATENT DOCUMENTS

WO WO 95/08945 4/1995

OTHER PUBLICATIONS

Extended European Search Report for Application No. 13190858.4, dated Feb. 19, 2014 (5 pages).
(Continued)

Primary Examiner — Daniel L Cerioni
Assistant Examiner — Yasmeen S Warsi
(74) Attorney, Agent, or Firm — Nixon Peabody LLP

(57) ABSTRACT

An endoscopic biopsy device for collecting samples. The device includes a tubular body having distal and proximal ends and jaws hinged to the distal end. The jaws operate between OPEN and CLOSED positions to secure a tissue sample. In the CLOSED position, the jaws define a sampling chamber. A collecting chamber for receiving samples is located within the body near the sampling chamber. A collecting member for transfixing secured samples is displaceable between a retracted position in the collecting chamber and a deployed position where the collecting member penetrates into the sampling chamber. The jaws include retaining elements projecting inwardly on a portion of the jaws. The retaining elements engage when the jaws are CLOSED, separating the sampling and collecting chambers from each other. The retaining elements disengage when the jaws are OPEN, providing a passage for the transfer of transfixed samples into and out of the collecting chamber.

20 Claims, 5 Drawing Sheets

(51) Int. Cl.
*A61B 10/06* (2006.01)
*A61B 1/018* (2006.01)
*A61B 17/32* (2006.01)

(52) U.S. Cl.
CPC ...... *A61B 10/06* (2013.01); *A61B 2010/0225* (2013.01); *A61B 2010/045* (2013.01); *A61B 2017/320064* (2013.01)

(56) References Cited

U.S. PATENT DOCUMENTS 5,762,069 A    6/1998  Kelleher
7,445,603 B2 * 11/2008 Zimmon ................ A61B 10/06
                                                    600/564

OTHER PUBLICATIONS

International Preliminary Report on Patentability, PCT/EP2014/073089, dated May 12, 2016 (7 pages).
Written Opinion of the International Searching Authority, PCT/EP2014/073089, dated Jan. 22, 2015 (6 pages).

* cited by examiner

ENDOSCOPIC DEVICE FOR MULTIPLE SAMPLE BIOPSY

CROSS-REFERENCE TO RELATED APPLICATIONS

This application is a U.S. National Stage of International Application No. PCT/EP2014/073089, filed Oct. 28, 2014, which claims the benefit of European Patent Application No. 13190858.4, filed Oct. 30, 2013, both of which are incorporated herein by reference in their entireties.

TECHNICAL FIELD

The present invention relates in one aspect to an endoscopic biopsy device for collecting multiple tissue samples. In a further aspect, the invention relates to an endoscopic biopsy instrument comprising such a device. In yet a further aspect, the invention relates to a method for taking multiple tissue samples using an endoscopic biopsy instrument.

BACKGROUND

When performing gastro-intestinal (GI) endoscopy, it is typically desired to take tissue samples at the same time. This may be achieved by advancing an endoscopic biopsy instrument through the instrument-channel of a GI endoscope to take a tissue sample. In order to be able to do so, the endoscopic biopsy instrument has to fulfil very stringent conditions as to the dimensions and remote operability through a long and narrow instrument-channel. The instrument-channel is typically between 2-4 mm, or even between 1-2 mm in ultrathin endoscopes. At the same time, typical GI endoscopes have a length of about 1-2 m or even more. Furthermore when operated, the GI endoscope, and thus also the endoscopic biopsy instrument when inserted through the instrument channel, has to follow a long tortuous path through the gastro-intestinal tract in order to reach the site of investigation and sample-taking. An endoscopic biopsy instrument therefore has a functional device for taking tissue samples, which is located at a distal end of an elongate, flexible shaft. The functional device and a distal portion of the elongate flexible shaft are dimensioned and configured to be inserted into and follow the instrument channel. The functional device is remotely operable by means of operating controls located at a proximal end of the elongate, flexible shaft extending outside the endoscope (and thus outside the patient), wherein the operating controls communicate mechanically with the functional device through the elongate, flexible shaft. Typically, the operating controls are combined in an operating handle at the proximal end of the endoscopic biopsy instrument. The functional device is a biopsy device for taking tissue samples from a bodily cavity, more particular for taking tissue samples from the inside of the GI tract.

One problem of common biopsy instruments is that they have to be removed from the instrument channel after each biopsy in order to recover the tissue sample. This results in a time consuming procedure when several tissue samples have to be secured from the same site and/or different sites. In practice, this also limits the number of tissue samples that can be taken from a patient during a given endoscopic examination session, and may therefore require more than one session in order to obtain a sufficient number of tissue samples. Furthermore, the examination may require that a plurality of tissue samples be collected around the same location. When having to remove the biopsy instrument after each sample taking, it may be difficult to precisely control and map the exact location of each tissue sample, and of the different tissue samples with respect to each other.

This problem is addressed by endoscopic instruments for multiple sample biopsy that are adapted to collect multiple tissue samples without having to remove the instrument from the body between samples. WO 95/08945 discloses an endoscopic instrument for obtaining a series of multiple tissue samples without being withdrawn from the endoscope. The instrument comprises jaws that are operable to secure a tissue sample. In one aspect the instrument comprises a needle-shaped retractor constructed to accumulate a series of tissue samples. The retractor is operated to pierce a newly secured sample for picking up the sample. However, previously collected samples press against the new sample, thus affecting reliability of the pick-up.

A further problem of such endoscopic biopsy instruments that are intended for use in narrow instrument channels is to obtain a reliable remote operation, in particular when the endoscope is inserted into a body cavity along a tortuous path. Furthermore, the tough spatial constraints make it very difficult to implement more advanced/complex functionality that may require a plurality of wires and/or flexible push rods for the transmission of operation control forces to the functional device.

Object of the present invention is to provide an endoscopic biopsy device/instrument for securing and collecting multiple tissue samples that overcomes problems of the prior art, provides an improvement or at least an alternative.

SUMMARY OF THE INVENTION

According to one aspect, the invention relates to an endoscopic biopsy device for collecting multiple tissue samples, wherein the endoscopic biopsy device comprises
- a tubular body having in an axial direction a distal end and a proximal end;
- jaws that are attached to the distal end of the body, wherein the jaws are moveable with respect to each other between an OPEN position and a CLOSED position to secure a tissue sample, and wherein the jaws in the CLOSED position define a sampling chamber;
- a collecting chamber for receiving multiple tissue samples, the collecting chamber being located within the body in a proximal direction adjacent to the sampling chamber;
- an axially extending collecting member for transfixing secured tissue samples, the collecting member being axially displaceable between a retracted position in the collecting chamber and a deployed position where the collecting member penetrates into the sampling chamber; and
- retaining elements that are moveable between an ENGAGED position and a DISENGAGED position, wherein the retaining elements in the ENGAGED position separate the sampling chamber and the collecting chamber from each other so as to prevent the transfer of transfixed samples past the retaining elements, while allowing for the collecting member to pass/penetrate, and wherein the retaining elements in the DISENGAGED position provide a passage for the transfer of transfixed tissue samples into and out of the collecting chamber.

Both actuated and non-actuated movement of the retaining elements can be conceived, wherein actuation refers to remotely controlled movement through means coupled to the element to be moved, such as traction wires or a linkage connected to the retaining elements for controlling their movement.

According to a preferred aspect, the invention relates to an endoscopic biopsy device for collecting multiple tissue samples, wherein the endoscopic biopsy device comprises a tubular body having in an axial direction a distal end and a proximal end;

jaws that are attached to the distal end of the body, wherein the jaws are moveable with respect to each other between an OPEN position and a CLOSED position to secure a tissue sample, and wherein the jaws in the CLOSED position define a sampling chamber;

a collecting chamber for receiving multiple tissue samples, the collecting chamber being located within the body in a proximal direction adjacent to the sampling chamber;

an axially extending collecting member for transfixing secured tissue samples, the collecting member being axially displaceable between a retracted position in the collecting chamber and a deployed position where the collecting member penetrates into the sampling chamber;

and wherein the jaws comprise retaining elements arranged to project radially inward on a proximal portion of the jaws, wherein the retaining elements engage to separate the sampling chamber and the collecting chamber from each other when the jaws are in the CLOSED position, and wherein the retaining elements disengage to provide a passage for the transfer of transfixed tissue samples into and out of the collecting chamber when the jaws are in the OPEN position.

In the context of the present application, the term "sample" refers to "tissue sample". The endoscopic biopsy device, and accordingly an endoscopic biopsy instrument comprising the endoscopic biopsy device, has a longitudinal axis. When inserted in an endoscope, the longitudinal axis of the endoscopic device/instrument is parallel to the longitudinal axis of the instrument channel of the endoscope. Since the endoscope, when in use, has to follow a bent path, the term "parallel" is here to be understood when considering a particular point/section, i.e. the longitudinal axis of the endoscopic device/instrument essentially follows the longitudinal axis of the endoscope. Beyond the distal end interface of the endoscope or the instrument channel, the respective longitudinal axis may be extrapolated by the tangent to that longitudinal axis at the point of the end interface. The terms "proximal" and "distal" are defined with respect to an operator's view of the endoscopic instrument, i.e. "proximal" refers to the operating/controlling end, whereas "distal" refers to the functional end. Axial directions are parallel to the longitudinal axis, wherein a distal direction is the axial direction towards the distal end, and a proximal direction is the axial direction towards the proximal end. The terms "radial" and "transverse" are also to be considered at a given point/section and refer to directions having a component perpendicular to the axial direction of that given point/section.

The tubular body is hollow, and is preferably elongate in the axial direction. The tubular body thus defines a frame and/or casing for the endoscopic biopsy device, and includes an internal cavity. Preferably, the tubular body has a circular cross-section as seen in a transverse cross-sectional plane. Further preferably the internal cavity has a circular cross-section as seen in a transverse cross-sectional plane. However, it may also be conceived that the transverse cross-sectional contours of the outer periphery and/or of the internal cavity at least section-wise follow other shapes, such as elliptical, polygonal or a combination thereof. In order to be suited for endoscopic biopsy, the device has to be dimensioned such that it can be passed through the instrument channel of an endoscope. The transverse dimensions of the tubular body are therefore not to exceed the transverse dimensions of the instrument channel in order to allow for passing the endoscopic biopsy device through the instrument channel of the endoscope. Typically, the tubular body is made of a relatively stiff material. In this case the following geometric considerations apply in order to configure the endoscopic biopsy device for a given endoscopic application. The dimension of the device in the axial direction is limited by the condition that the device can be passed through the instrument channel around typical bends as occurring during endoscopic examinations of the given application, here in particular endoscopic examinations of the GI tract. The allowable transverse dimension and the allowable length of the tubular body may be configured depending on the geometry of the instrument channel and the minimum bending radii for a given endoscope. The skilled person is thus instructed to adapt the absolute value of the transverse dimension of the tubular body and the aspect ratio of the transverse and longitudinal dimensions of the tubular body according to beforehand specified lumen dimensions and the minimum bending radius of the instrument channel of a given/specified endoscope. Typical values for the total transverse clearance between the inner wall of an instrument channel and the outer wall of the endoscopic biopsy device are a few tenths of millimeters, and typical values for the length of the endoscopic biopsy device are a few centimeters, wherein the dimensions of the tubular body have to fit within these constraints. According to an advantageous embodiment, the tubular body may comprise a stiff section and a flexible section in axial extension thereof. The shape of the stiff section essentially does not change to follow the bended shape of the instrument channel and therefore has to fulfil the above-mentioned geometric considerations. As above, the stiff section provides a frame and/or casing for the mechanics of the biopsy device. The flexible section is configured to elastically deform to follow any bends of the endoscope. The length of the flexible section is therefore not limited by the above-mentioned geometric considerations. By providing a stiff section and a flexible section, an increased length and thus an increased volume of the tubular body may be achieved without affecting the applicability for a given geometry in an endoscopic application. In a further development of this embodiment, the tubular body may also be constructed from alternating stiff and flexible sections and/or a series of stiff sections that are flexibly linked together by articulated joints. Again, the stiff sections have to fulfil the above-mentioned geometric considerations. An extended volume of the tubular body is e.g. desirable, when the lumen of the tubular body comprises the collecting chamber, thereby increasing the capacity of the device for holding multiple tissue samples. In an advantageous embodiment, the distal end of the tubular body is made of a stiff section, wherein the adjacent flexible section is arranged on the proximal side of the stiff section, and wherein the distal side of the stiff section carries the jaws of the biopsy device.

The jaws are operable between an OPEN position and a CLOSED position to secure a sample. Typically, a site of particular interest is identified by visual inspection through the endoscope. The biopsy device is then advanced through the instrument channel of the endoscope to the site of interest, wherein the biopsy device projects at least partially from the instrument channel at the distal end of the endoscope. The biopsy device may be introduced into the endoscope before introducing the endoscope into the cavity to be inspected/examined or after the endoscope has been introduced. Preferably, if possible, the biopsy device is kept within the field of view of the endoscope in order to visually follow, supervise, capture and/or record the sample taking process.

To secure a sample, the jaws are opened, advanced to the tissue to be sampled, and then closed to sever a sample of the tissue in a known manner. Advantageously according to one embodiment of the endoscopic biopsy device, however, no cutting action is performed for obtaining a sample in a GI endoscopic procedure in order to avoid punctuation of the intestinal wall. In this embodiment, preferably the jaws have blunt edges, preferably meeting in the CLOSED position with a slight clearance of less than 0.2 mm, preferably less than 0.1 mm. To secure a sample using this embodiment, the jaws are opened, advanced to the tissue to be sampled, and then closed to take a firm grip of the tissue. The biopsy device is then retracted in a swift movement to tear off the tissue sample. In any case, the secured sample is enclosed in the sampling chamber defined by the jaws in the CLOSED position. To define a sampling chamber, at least one, and preferably all of the jaws are concave towards the inside so as to form an internal cavity at the distal end of the endoscopic biopsy device when the jaws are closed.

The endoscopic biopsy device has at least two jaws. In a preferred embodiment, at least two jaws are movably attached to the body at the distal end and adapted to cooperate with each other for the taking of tissue samples. Alternatively, at least a first jaw may be fixed with respect to the body, e.g. formed by a distally projecting portion of the body, and at least a second jaw is movably attached to the body at the distal end and adapted to cooperate with the first jaw for the taking of tissue samples.

Adjacent to the sampling chamber on a proximal side thereof, a collecting chamber is provided. The collecting chamber extends from the sampling chamber in a proximal direction into the internal cavity of the tubular body. The collecting chamber is adapted to receive a plurality of tissue samples stacked in the axial direction. Typically, the collecting chamber is elongate in the axial direction, and typically extends through most of the tubular body up to a coupling section at the distal end of the endoscopic biopsy device. The coupling section is adapted to connect the endoscopic biopsy device to the distal end of a shaft of an endoscopic biopsy instrument. The coupling section comprises suitable means for securing the endoscopic biopsy device to the shaft and for interconnecting the device functions with the shaft transmission in order to communicate with operation controls arranged at the proximal end of the shaft. Typically, the coupling is fixed. However, embodiments with a detachable coupling may also be conceived.

The collecting member extends in an axial direction and is displaceable along the axial direction between a retracted position and a deployed position. In the retracted position, the collecting member is located within the collecting chamber, whereas the collecting member in the deployed position projects into the sampling chamber, or even penetrates through the sampling chamber. In one embodiment, the collecting member may in the deployed position even project through an opening/gap/aperture in or between the jaws, and beyond the distal end of the endoscopic biopsy device. The retracted position is chiefly intended for the storage of tissue samples in the collecting chamber. Positions of deployment are chiefly intended for steps of picking up newly secured tissue samples from the sampling chamber. The collecting member is configured for transfixing the collected tissue samples, and for holding these samples for storage within the endoscopic device.

Furthermore, in some procedures, the collecting member may also be used for anchoring the endoscopic biopsy device at a particular location in the tissue to be sampled. To that end, the endoscopic device is advanced to the location, and the collecting member is deployed to a far distal position so as to pierce the tissue to be sampled. Subsequently, the jaws are operated for securing a tissue sample from that particular location.

The collecting member has a free end pointing in the distal direction. The free end has a pointed/sharpened tip allowing for piercing the tissue sample. At the proximal end, the collecting member is supported in a way that allows for controlling the displacement/movement of the collecting member during operation. Preferably, the collecting member is displaced back and forth in a linear translational movement along the axial direction. However other movements for deploying and retracting the collecting member may be conceived. For example, the movement in the axial direction may be superimposed with a rotational movement around the longitudinal axis, thereby obtaining a helicoidal screw movement in the axial direction. Once a new tissue sample has been secured in the sampling chamber by operating the jaws, the jaws are kept in the CLOSED position, and the collecting member is deployed in a distal direction into the sampling chamber and through the tissue sample, thereby transfixing the tissue sample. The transfixed sample is transferred to the collecting chamber for storage, by retracting the collecting member.

Retaining elements are arranged at a proximal end of the sampling chamber and at a distal end of the collecting chamber. The retaining elements are moveable between an ENGAGED position and a DISENGAGED position. In the DISENGAGED position, the retaining elements provide a passage for the transfer of transfixed tissue samples into and out of the collecting chamber. Transfer of transfixed tissue samples between the sampling chamber and the collecting chamber is therefore performed with the retaining elements in the DISENGAGED position. In the ENGAGED position, the retaining elements engage around the path of displacement of the collecting member, wherein the engaged retaining elements leave an opening for the collecting member to pass, such that the collecting member can still be deployed and retracted. The opening between the engaged retaining elements does not, however, allow for the passage of tissue samples held by the collecting member. When deploying the collecting member through the engaged retaining elements and into the sampling chamber, already transfixed samples are thus pushed against the proximal side of the retaining elements, thereby retained in the collecting chamber and shifted towards the proximal end of the collecting member. By providing retaining elements that define separate sampling and collecting chambers, the process of obtaining a tissue sample is separated from the safe-keeping of tissue samples. Furthermore, the location of the retaining elements at the proximal end of the sampling chamber is advantageous, since the required displacement of the collecting member for shifting the collected tissue samples towards the proximal end and free the collecting member tip for securing a new tissue sample is reduced as compared to other constructions. Using this endoscopic biopsy device, multiple tissue samples are sluiced one by one through the sampling chamber into the collecting chamber.

A further advantage of the retaining elements is achieved when performing a procedure where the endoscopic biopsy device is anchored in the tissue to be sampled by deploying the collecting member prior to operating the jaws for securing the tissue sample. By shifting any previously collected samples towards the proximal end as described above, the tip of the collecting member is freed from any tissue samples and is thus again freely available for anchoring the endoscopic device at the next location in the tissue to be sampled.

According to the above-mentioned preferred embodiment, retaining elements are arranged on a proximal portion of the jaws. The retaining elements project radially inward from the inside of the jaws. The retaining elements engage when the jaws are in the CLOSED position, thereby defining a proximal end of the sample chamber and a distal end of the collecting chamber. The retaining elements disengage when the jaws are in the OPEN position so as to provide a passage for the transfer of transfixed tissue samples into and out of the collecting chamber. Transfer of transfixed tissue samples between the sampling chamber and the collecting chamber is therefore performed with the jaws in the OPEN position.

As mentioned above, both actuated and non-actuated movement of the retaining elements can be conceived. According to one embodiment with non-actuated retaining elements, the retaining elements are spring-loaded and biased to the ENGAGED position against a limit stop preventing disengagement of the retaining elements by an axial force applied to the retaining elements in the distal direction, whereas the retaining elements are moveable from the ENGAGED position to the DISENGAGED position by the application of an axial force applied to the retaining elements in the proximal direction. Thereby a "check-valve" function of the retaining elements is achieved allowing for the unidirectional transfer of secured samples from the sampling chamber to the collecting chamber. A secured sample is transfixed by deploying the collecting member. When retracting the collecting member, the transfixed sample pushes in a proximal direction against the retaining elements, thereby disengaging the retaining elements to allow for the transfer of the transfixed sample in the proximal direction from the sampling chamber into the collecting chamber. Once the transfixed samples are in the collecting chamber, the retaining elements return to the ENGAGED position and work like a check valve or a fish trap preventing the collected samples from leaving the collecting chamber again. When the collecting member is deployed again in order to transfix a newly secured sample, the previously collected samples push the retaining elements in a distal direction against the limit stop.

For example in one embodiment, the retaining elements may be flaps that are hinged to the tubular body and by means of a spring biased against a limit stop to the ENGAGED position where they project radially inward. The limit stop prevents opening of the flaps in a distal direction, whereas the flaps may be opened (disengaged) in a proximal direction against the bias of spring. After the multiple sample biopsy procedure has been concluded, the collected tissue samples have to be retrieved from the collecting chamber. Retrieval of the collected tissue samples in a distal direction, through the open jaws may then be achieved by applying an external force in a proximal direction on the retaining elements, e.g. using an adequate tool, so as to disengage the retaining elements and allow for the transfer of the collected tissue samples out of the collecting chamber. By this embodiment with non-actuated retaining elements, a sluicing function is achieved without significantly increasing the complexity of the device, and in particular without increasing the complexity of the device control. According to another embodiment the retaining elements are actuated, e.g. by dedicated traction wires and/or push rods, or may be coupled to jaw actuation by means of a linkage. In the above-mentioned preferred embodiment, the retaining elements are fixed to the jaws, and the operation of the retaining elements is thus directly coupled to the operation of the jaws. Thereby an embodiment with actuated retaining elements is achieved without increasing the complexity of the required actuation/control of the endoscopic biopsy device.

Further according to one embodiment of the endoscopic biopsy device, the retaining elements are formed as a transversely oriented partition. Preferably, each jaw comprises separation walls arranged in a transverse plane with respect to the axial direction, wherein the separation walls engage around the path of displacement of the collecting member, and cooperate to form a partition wall between the sampling chamber and the collecting chamber, leaving a central aperture or slots for the collecting member to pass. However, it may also be conceived that the partition is formed by inwardly projecting elements provided only on one/some of the two or more jaws, as long as the thus provided retaining elements engage when the jaws are in the CLOSED position, and disengage when the jaws are in the OPEN position.

Further according to one embodiment of the endoscopic biopsy device, the jaws are hinged to the body by pivot-joints. Preferably all of the jaws are hinged to the body in order to allow for a symmetric operation of the jaws. Two or more hinged jaws are conceivable. However, for the sake of simplicity of the construction, embodiments with pivot-joints typically have a two-fold symmetry with two symmetrically acting jaws.

Further according to one embodiment of the endoscopic biopsy device, the jaws are hinged to the body by axially extending tongue-shaped flexible joints. Also in this embodiment, embodiments with two or more jaws are conceivable. The embodiment is advantageous in that the hinges and even the jaws may be produced from the same tubular piece that also forms the body, by partially cutting said tubular body in an axial direction from the distal end, thereby obtaining axially extending tongue shaped flexible joints separated from each other by axially extending slits. The flexibility of the joints may be controlled, e.g. by adjusting the width of the tongues. The flexibility of the joints may be further controlled by adjusting the thickness of the walls, e.g. by controlled thinning of the walls of the tubular body in the region of the tongues. This embodiment reduces the number of parts in the jaw assembly, thereby simplifying the construction, in particular for embodiments with a larger number of jaws, such as three or four jaws, which may be linked together for simultaneous actuation using a single operating control. Preferably, the jaws are arranged to be operated in an essentially symmetric manner.

Further according to one embodiment of the endoscopic biopsy device, the flexible joints are outwardly biased springs. Thereby a simplified mechanism is achieved where only the closing of the jaws needs actuation, e.g. by sliding an outer sleeve over the jaws, wherein the inner diameter of the sleeve corresponds to the outer diameter of the jaws in the CLOSED position. The jaws are opened by sliding the sleeve in an axial direction to a proximal position such that the jaws due to their bias can freely expand to the OPEN position. The jaws are closed by sliding the sleeve in the opposite direction to a distal position, thereby constraining the jaws against their bias to the CLOSED position. Also in this embodiment, the jaws are provided with inwardly projecting retaining elements separating a sampling chamber from the collecting chamber as discussed above.

Further according to one embodiment of the endoscopic biopsy device, cooperating edges of the jaws are blunt. The edges may be dulled, e.g. by providing a chamfer, bevel and/or rounding of the edges at the scale of the peripheral walls of cooperating jaws. Thereby, damage to underlying tissue, which should not be sampled, is avoided.

Endoscopic biopsy device according to any of the preceding claims, wherein the jaws along their cooperating edges are provided with a serrated, toothed and/or waved profile. Thereby the gripping function of cooperating jaws is improved. Preferably, the edges and/or features of the serrated, toothed and/or waved profile are blunt at the scale of the profile so as to improve gripping action while at the same time avoiding damage to underlying tissue, which should not be sampled.

Further according to one embodiment of the endoscopic biopsy device, the collecting member is a needle, the needle tip pointing in a distal direction. The collecting member is preferably shaped as a spike/spear/skewer/needle-like element with a rod portion that is terminated by a pointed/sharpened tip at the distal end. On an element of the needle-shaped type, the sample is pierced by the pointed tip and pushed further onto the rod portion as the collecting member is advanced further in the distal direction, and the tissue sample is then held by the rod portion.

Further according to one embodiment of the endoscopic biopsy device, the collecting member is detachably coupled to an axially sliding stem, the stem being arranged proximally with respect to the body. The collecting member is preferably detachable in order to facilitate an easy retrieval of the collected samples. The collecting member may e.g. be detached and removed from the endoscopic biopsy device through the jaws in the OPEN position. The tissue samples may be retrieved immediately from the collecting member, indexed, and packaged for shipment/transfer to a laboratory for further pathological analysis. Alternatively, the entire collecting member with the collected samples on it may be packaged/labelled and transferred to the laboratory, and a new collecting member may be replaced for the used one in the endoscopic biopsy device. In the mounted position, the tip of the collecting member points in the distal direction. The collecting member is at its proximal end attached to and supported by a stem, which may slide in the axial direction, e.g. in a sliding bushing. The detachable coupling may for example be a threaded connection, a snap-fit engagement, or preferably a spring-clip secured connection. The stem may slide in the axial direction, e.g. in a sliding bushing. The collecting member is deployed by axially displacing the stem in a distal direction, i.e. towards the distal end of the endoscopic biopsy device. The collecting member is retracted by moving the sliding stem in a proximal direction opposite to the distal direction, i.e. towards the proximal end of the endoscopic biopsy device.

Further according to one embodiment of the endoscopic biopsy device, the collecting member comprises one or more of radially projecting protuberances, a barbed tip and a retro-serrate surface. The barbs, protuberances, projections and/or serrations are configured to keep samples fixed to the collecting member, preventing collected samples from falling off. The barbs, protuberances, projections and/or serrations are preferably shaped so as to facilitate a gentle penetration through the tissue sample during the transfixing procedure when collecting the multiple samples, to keep the collected tissue samples fixed on the collecting member, yet allowing for easy and gentle retrieval of the tissue samples from the collecting member. Preferably, this may be achieved by an asymmetric profile of the barbs, protuberances, projections and/or serrations as seen in an axially oriented cross-sectional plane, with a gentle sloping on the distal side of the profile and a steep, or even concavely inverted sloping on the proximal side of the profile.

Advantageously according to one embodiment, the barbs, protuberances, projections and/or serrations may follow a circumferentially helical path in combination with the above-mentioned asymmetric profile pointing in the proximal direction. This allows for gentle transfixing of a tissue sample by a purely translational axial movement, while allowing for retrieval of the transfixed tissue sample by "un-screwing" it from the collecting member.

Further according to one embodiment of the endoscopic biopsy device, the jaws are operated by traction wires. Traction wires can be made thinner than a mechanical connection that is also to be used as a push rod for transmitting pushing forces. The traction wires are therefore more flexible and take up less of the valuable cross-sectional space/lumen of the shaft/shaft lumen. Advantageously according to one embodiment, the number of traction wires to be passed to remote operating controls at a proximal end of the endoscope may be reduced by providing a linkage between simultaneously, and preferably also symmetrically, operated jaws.

A further aspect of the invention relates to an endoscopic biopsy instrument comprising an elongate flexible shaft, an endoscopic biopsy device according to any of the above-mentioned embodiments arranged at a distal end of the shaft, and operating controls arranged at a proximal end of the shaft, wherein a distal portion of the endoscopic biopsy instrument is configured for insertion into the instrument channel of an endoscope and wherein the operating controls are configured to communicate with the endoscopic biopsy device through the shaft to control operation of the endoscopic biopsy device.

Further according to one aspect, the endoscopic biopsy instrument is integrated with an endoscope, such as a GI-endoscope.

Further according to one embodiment of the endoscopic biopsy instrument, the endoscopic biopsy device is connected to the shaft via a detachable coupling.

Further according to one embodiment of the endoscopic biopsy instrument, the detachable coupling is a bayonet coupling.

A yet further aspect of the invention relates to a method of performing an endoscopic biopsy procedure for taking multiple tissue samples using an endoscopic biopsy instrument, the method comprising the steps of (a) advancing a distal portion of the endoscopic biopsy instrument through an instrument channel of an endoscope to a sampling site, (b) operating jaws located at a distal end of the endoscopic biopsy instrument to secure a tissue sample from the sampling site in a sampling chamber defined between the jaws in a CLOSED position, (c) engaging retaining elements arranged at a proximal end of the sampling chamber, (d) deploying a collecting member in a distal direction through the retaining elements, into the sampling chamber and through the tissue sample, thereby transfixing the tissue sample (e) disengaging the retaining elements so as to allow the transfixed tissue sample to pass between the retaining elements, and (f) retracting the collecting member in the proximal direction, thereby transferring the transfixed tissue sample to a collecting chamber, the collecting chamber being arranged in a proximal direction adjacent to the sampling chamber.

After retracting the collecting member in step (f), the retaining elements may be engaged so as to retain the already transfixed tissue sample in the collecting chamber.

By this method, the tissue sample is "sluiced" into the collecting chamber, by first obtaining the tissue sample and securing it in the sampling chamber, and subsequently collecting the sample from the sampling chamber and transferring it to the collecting chamber. Thereby the process of obtaining a tissue sample is separated from the safe-keeping of the tissue sample.

Advantageously according to a preferred embodiment, the operation of the retaining elements is coupled to the operation of the jaws, wherein the retaining elements are engaged when the jaws are in the CLOSED position and wherein the retaining elements are disengaged when the jaws are in the OPEN position.

Advantageously according to a preferred embodiment, the method is carried out using an endoscopic biopsy device/instrument according to any of the above-mentioned embodiments.

Further according to one embodiment, the above-mentioned method further comprises the steps of (g) moving the biopsy instrument to a further sampling site,
(h) operating the jaws to secure a further tissue sample from the further sampling site in the sampling chamber,
(i) engaging the retaining elements,
(j) deploying the collecting member in the distal direction through the engaged retaining elements, into the sampling chamber and through the further tissue sample, thereby transfixing the further tissue sample while retaining already transfixed tissue samples in the collecting chamber by means of the retaining elements acting against the displacement of the already transfixed tissue samples in the distal direction with the collecting member and shifting their position towards the proximal end of the collecting member,
(k) disengaging the retaining elements, and
(l) transferring the newly transfixed further tissue sample to the collecting chamber by retracting the collecting member in the proximal direction.

After retracting the collecting member in step (l), the retaining elements may be engaged so as to retain the tissue samples in the collecting chamber.

By this method, a "sluicing" of multiple tissue samples one by one through the sampling chamber into the collecting chamber is achieved. In particular, the process of obtaining a further tissue sample is separated from the safe-keeping of previously collected tissue samples that are already present in the collecting chamber. First, a further tissue sample is obtained and secured in the sampling chamber. Then, the further tissue sample is collected from the sampling chamber by means of a collecting member, which is deployed by from a retracted position in the collecting chamber to reach into the sampling chamber and transfix the new tissue sample on a distal end thereof. During that step, the jaws are kept in the CLOSED position in order to hold on to the newly secured sample in the sampling chamber and at the same time keeping the retaining elements engaged, separating the collecting chamber from the sampling chamber. Already collected tissue samples are held back in the collecting chamber by the retaining elements, since the retaining elements act against the displacement of the already transfixed tissue samples in the distal direction and shift the position of these tissue samples towards the proximal end of the collecting member. Once the newly secured sample is transfixed on the distal end of the collecting member, the retaining elements are disengaged, and the new sample is added to the collection by transferring it to the collecting chamber.

Further according to one embodiment, the above-mentioned method further comprises repeating steps (g)-(l) in order to collect one or more yet further tissue samples from one or more yet further sampling sites one by one. The steps for collecting multiple tissue samples may be repeated as often as necessary/desired until the holding capacity of the collecting chamber is reached. The stack of collected tissue samples may be compressed by advancing the collecting member with the retaining elements in the ENGAGED position, in order to press the collected tissue samples against the retaining elements, thereby increasing the number of tissue samples that can be collected without having to remove the endoscopic biopsy device from the endoscope.

Further according to one embodiment, the above-mentioned method further comprises removing the endoscopic biopsy instruments from the endoscope to retrieve collected tissue samples.

BRIEF DESCRIPTION OF FIGURES

Preferred embodiments of the invention will be described in more detail in connection with the appended drawings, which show in FIG. 1 a side cross-sectional view of an endoscopic device for multiple sample biopsy according to one embodiment, with OPEN jaws, FIG. 2 a side cross-sectional view of the device of FIG. 1, with CLOSED jaws, FIG. 3 (i)-(iv) a series of steps for collecting a tissue sample using the device of FIG. 1, FIG. 4 (i)-(iv) a series of steps for collecting a further tissue sample using the device of FIG. 1, FIG. 5, a side cross-sectional view of the device of FIG. 1 with multiple tissue samples, FIG. 6 the retrieval of multiple tissue samples from the collecting member, FIG. 7 a bottom elevation view of the device of FIG. 1, FIG. 8 a top elevation view of a further embodiment of an endoscopic device for multiple sample biopsy, FIG. 9 a side cross-sectional view of the device of FIG. 8 along line IX-IX, with the jaws in the OPEN position, and FIG. 10 a side cross-sectional view of the device of FIG. 8 with the jaws in the CLOSED position, FIG. 11 a view of a jaw for an endoscopic biopsy device according to one embodiment, and FIG. 12 a view of a jaw for an endoscopic biopsy device according to another embodiment.

DETAILED DESCRIPTION

FIGS. 1-7 show different views of an endoscopic biopsy device 1 for the collection of multiple tissue samples 100, 101, 102, 103, 104 (10*x*). In the side cross-sectional views of FIGS. 1-6, the cross-sectional plane is parallel to the axial direction and passes through a central axis of the device 1.

Figure 1:
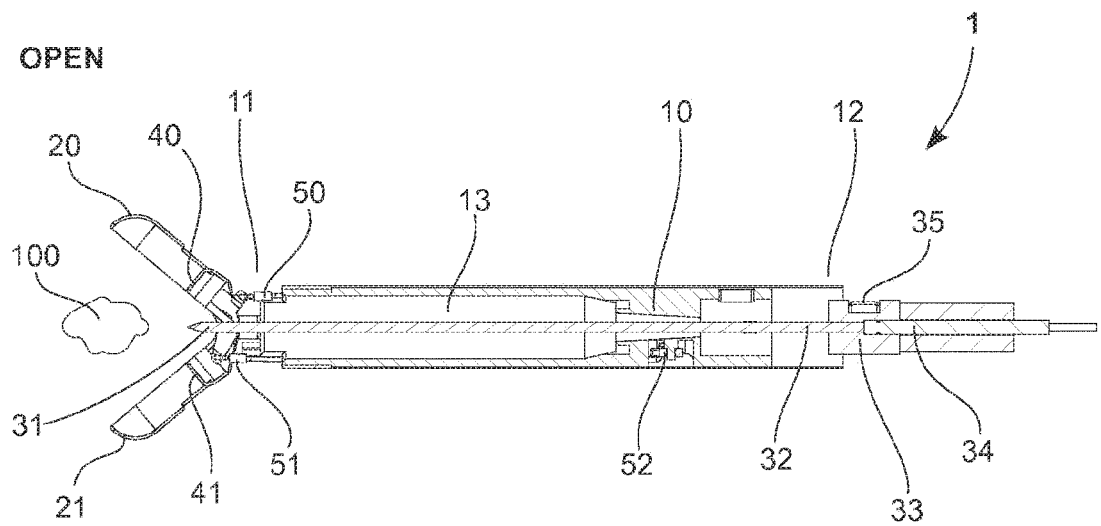
Figure 2:
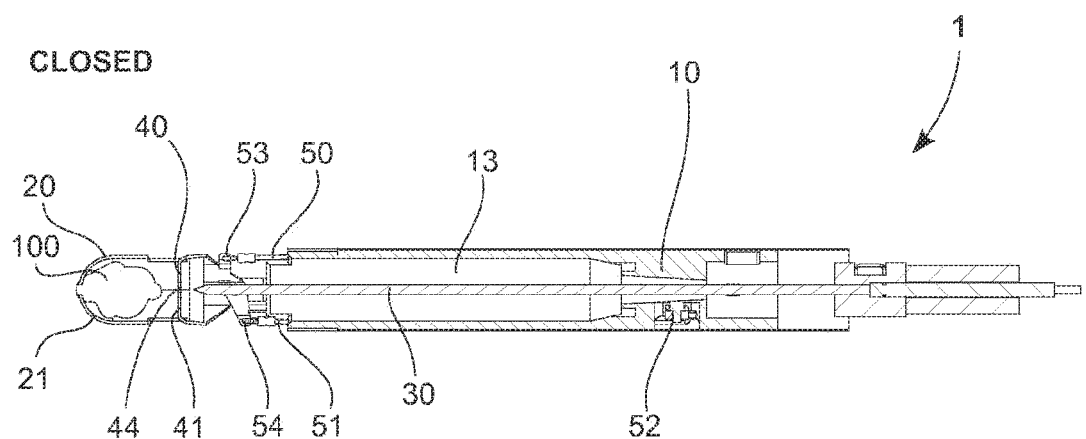
Figure 7:
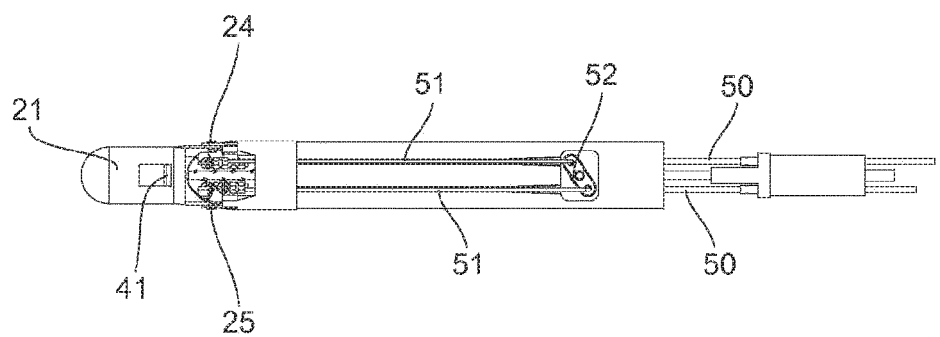

Referring to FIGS. 1, 2 and 7, the endoscopic biopsy device 1 comprises an elongate tubular body 10 extending in an axial direction from a distal end 11 to a proximal end 12, wherein the axial direction is parallel to the longitudinal axis of the tubular body 10. The tubular body 10 has an internal cavity with an opening at the distal end 11. The internal cavity defines a collecting chamber 13 for receiving multiple tissue samples 10*x*.

At a distal end, the endoscopic biopsy device 1 comprises two half-shell shaped jaws 20, 21 with their concave side facing to each other. The jaws 20, 21 are hinged to the distal end 11 of the body 10 by means of a pivot joint 24 (see FIG. 7) with a pivot axis perpendicular to the cross-sectional plane of FIGS. 1-5. The jaws 20, 21 are moveable with respect to each other between an OPEN position as shown in FIG. 1, and a CLOSED position as shown in FIG. 2. In the CLOSED position, the jaws 20, 21 define a sampling chamber 23.

The endoscopic biopsy device 1 further comprises a needle-shaped collecting member 30. The collecting member 30 is arranged parallel to the axial direction, on the central axis of the tubular body 10. At a distal end 31, the collecting member 30 has a needle tip pointing in the distal direction. Preferably, the collecting member is provided with barbs/retroserrations/protuberances, not shown in the drawing. The tips of the barbs and/or retroserrations are designed to point in a proximal direction away from the needle tip, so as to prevent transfixed samples from sliding off the needle. At a proximal end 32, the collecting member 30 is detachably connected to a stem 34 by means of a coupling 33 with a spring-clip 35. The stem 34 is slidable in the axial direction, thereby operating the collecting member 30 in a linear translational movement along the axial direction. The collecting member 30 is deployed by moving the stem 34 in the distal direction, and retracted by moving the stem 34 in the proximal direction.

On a proximal portion of the jaws 20, 21, retaining elements 40, 41 are provided pointing radially inward. The retaining elements 40, 41 engage when the jaws 20, 21 are in the CLOSED position, and disengage when the jaws 20, 21 are in the OPEN position. Advantageously, the retaining elements 40, 41 may be produced from the peripheral wall of the half-shell shaped jaws 20, 21, e.g. by cutting an appropriate shape, leaving a transversely oriented side of the shape connected, and bending the shape towards the inside of the half-shell to point radially inward. When engaged, the retaining elements 40, 41 define a proximal end of the sampling chamber 23 and form a transversely oriented partition separating the sampling chamber 23 from the collecting chamber 13. The retaining elements 40, 41 are shaped, when engaged, to leave a central aperture 44 for the collecting member 30 to pass. When disengaged, the retaining elements 40, 41 open a passage for tissue samples 100 to enter the collecting chamber 13.

The jaws 20, 21 may be remotely actuated to open and close by means of traction wires 50 connected to primary jaw levers with eyelets 53. A linkage provided via link joint 52 and wires 51 connected to secondary jaw levers with eyelets 54 connects/synchronizes the movement of the jaws 20, 21. The linkage allows for opening the two jaws 20, 21 by one traction wire 50, and further closing the jaws 20, 21 with one further traction wire 50, and avoid crossing of any of the operating wires 50, 51. The jaws 20, 21 are thus operable to grasp around a sample 100 and secure the sample 100 inside the sampling chamber 13.

Figure 3:
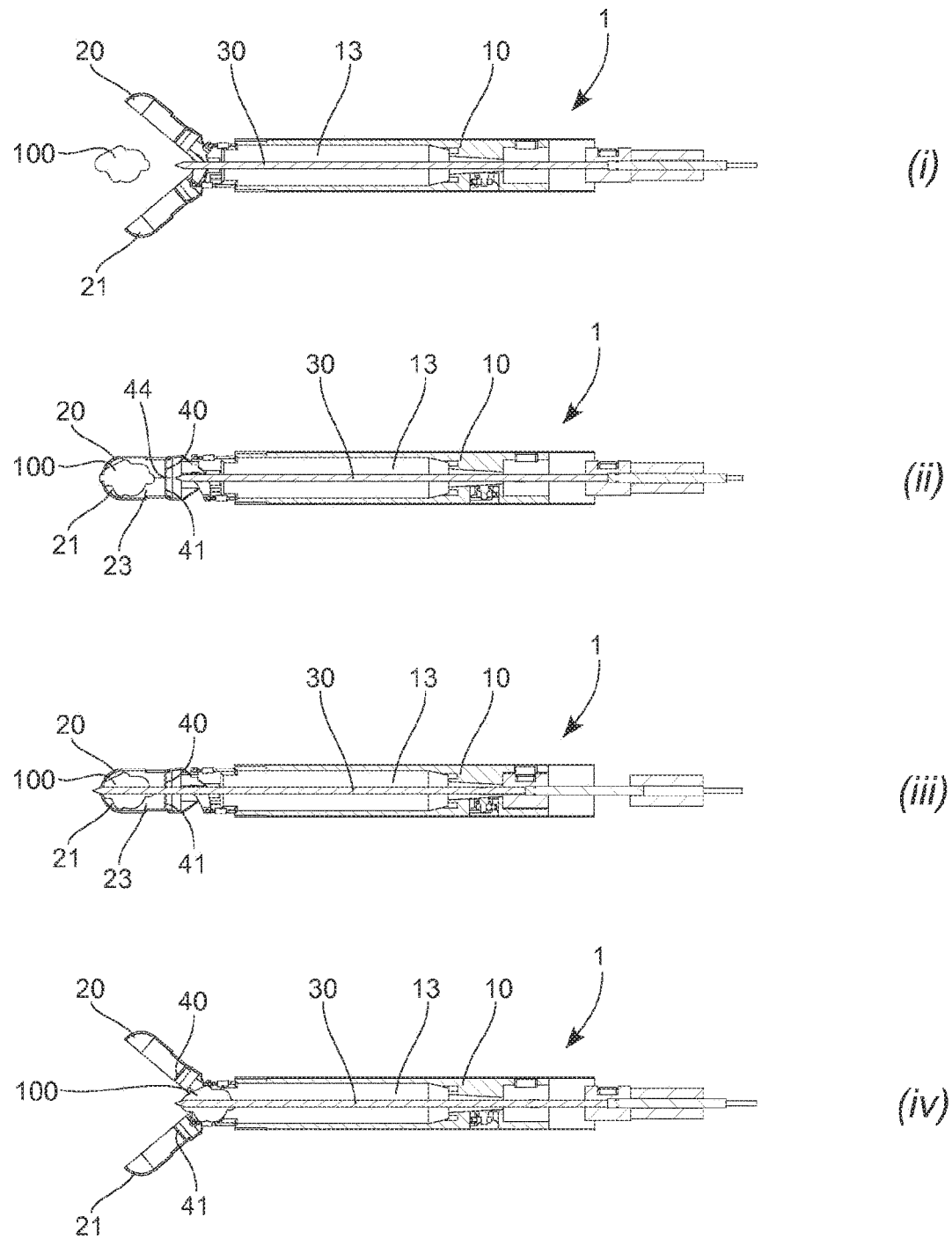

FIG. 3 shows a sequence of steps (i)-(iv) illustrating the securing and collecting of a tissue sample 100 using the above-described endoscopic biopsy device 1: (i) the endoscopic biopsy device 1 approaches a tissue sample 100 with open jaws 20, 21 and the collecting member 30 in a retracted position; (ii) the tissue sample 100 has been secured inside the sampling chamber 23 defined by the jaws 20, 21 in the CLOSED position, with the retaining elements 40, 41 engaged, and the collecting member 30 still in the retracted position; (iii) the jaws 20, 21 are maintained in the CLOSED position, the retaining elements 40, 41 are engaged, and the collecting member has now been deployed through the central aperture 44, thereby transfixing the sample 100 onto the collecting member 30; (iv) the jaws 20, 21 are in the OPEN position, the retaining elements are disengaged, and the collecting member 30 has been retracted, thereby transferring the transfixed sample 100 into the collecting chamber 13 inside the tubular body 10.

Figure 4:
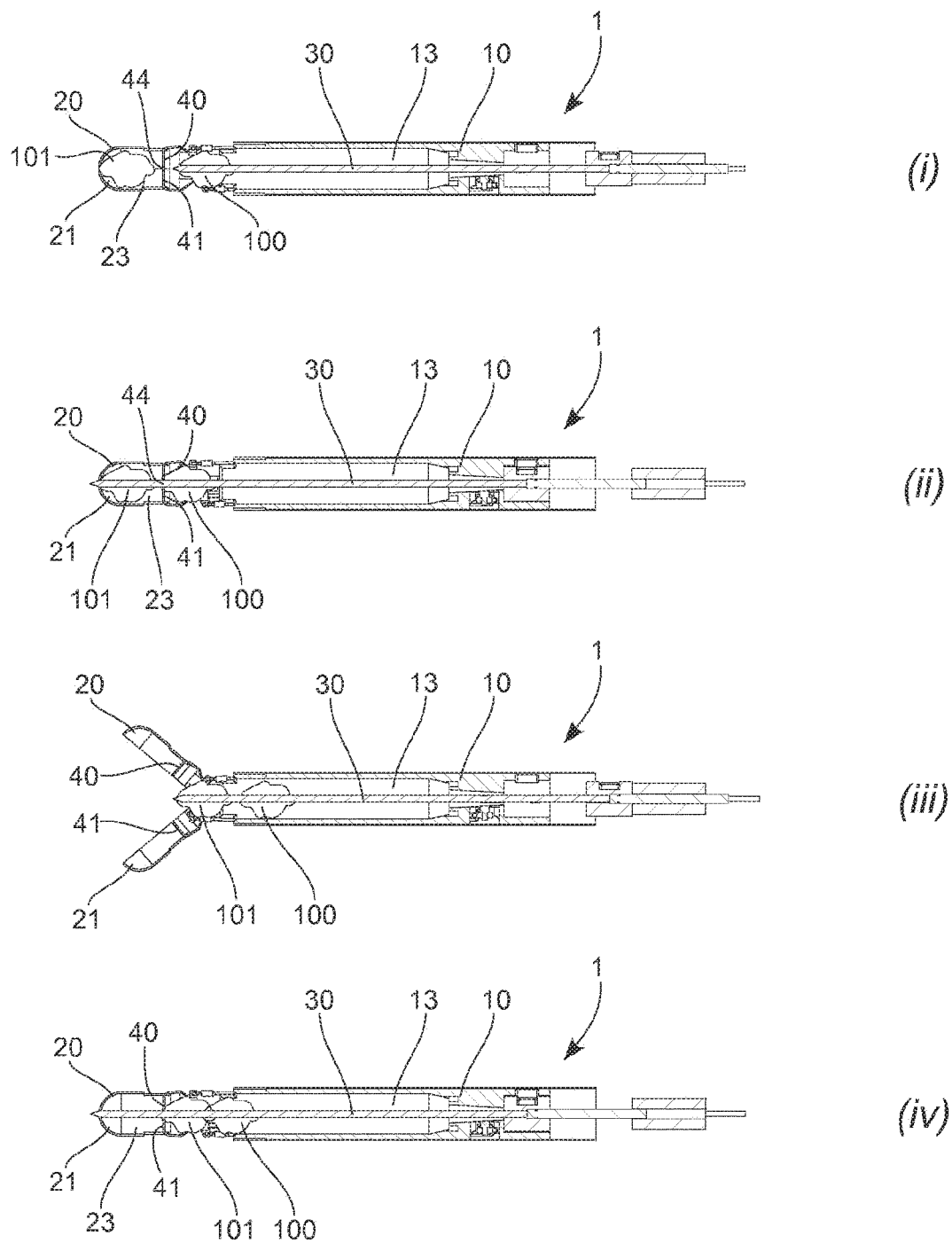

FIG. 4 shows a sequence of steps (i)-(iv) illustrating the securing and collecting of a further tissue sample 101, in addition to an already collected tissue sample 100, using the above-described endoscopic biopsy device 1: (i) the endoscopic biopsy device 1 holds an already collected tissue sample 100 transfixed on the collecting member 30 inside the collecting chamber 13, and a further tissue sample 101 is secured in the sampling chamber 23; (ii) the collecting member 30 has been deployed through the aperture 44 in the engaged retaining elements 40, 41, thereby pushing the first tissue sample 100 against the proximal side of the retaining elements, shifting the position of the first sample 100 towards the proximal end of the collecting member 30, and transfixing the further tissue sample 101; (iii) the retaining elements 40, 41 are disengaged by opening the jaws 20, 21, and the newly transfixed tissue sample 101 is transferred into the collecting chamber 13 by retracting the collecting member 30; (iv) by deploying the collecting member 30 with the jaws 20, 21 in the CLOSED position, the collected tissue samples 10*x* are pushed against the engaged retaining elements 40, 41, thereby compacting the stack of multiple tissue samples 10*x* and shifting their position towards the proximal end of the collecting member 30.

Figure 5:
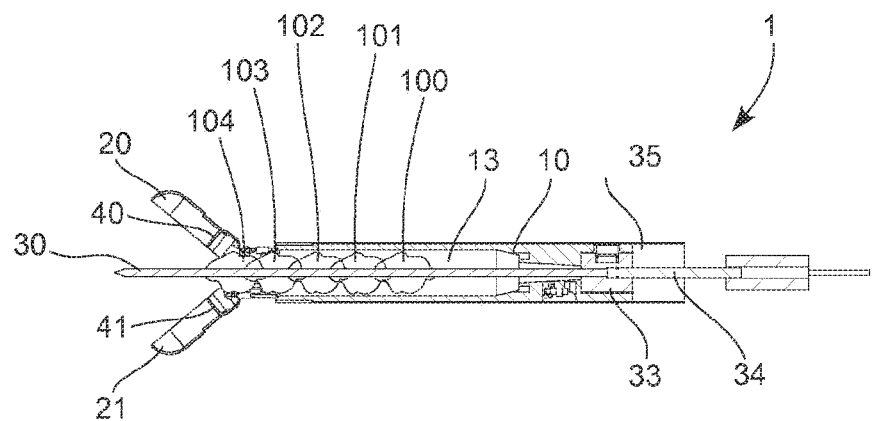
Figure 6:
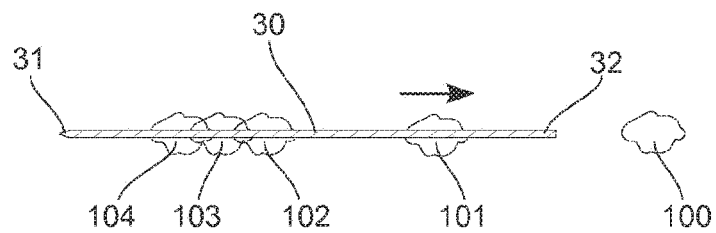

FIGS. 5 and 6 show the retrieval of multiple tissue samples 10*x* from the above-described endoscopic biopsy device 1. The jaws 20, 21 are moved to the OPEN position and the retaining elements 40, 41 thereby disengaged. The coupling 33 with spring-clip 35 is released, the collecting member 30 is detached from the stem 34, and the collecting member 30 with the multiple samples 10*x* transfixed thereon is removed from the distal end through the open jaws 20, 21. Once the needle-shaped collecting member 30 is removed from the endoscopic biopsy device 1, the samples 10*x* can be pushed off the needle one by one. In order to easily remove the tissue samples 10*x* and to avoid damaging them, the samples 10*x* are preferably pushed off following the direction of any barbs and retroserrations provided on the collecting member 30, i.e. in the proximal direction from the distal end 31 towards the proximal end 32 of the collecting member 30.

Figure 8:
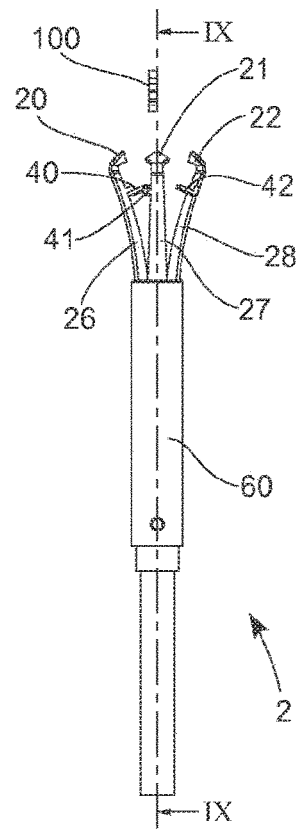
Figure 9:
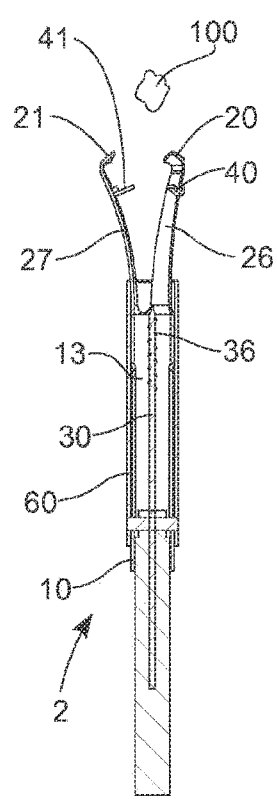
Figure 10:
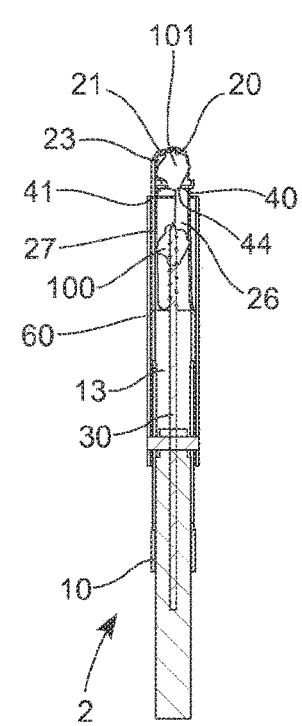

FIGS. 8-10 show another embodiment of an endoscopic biopsy device 2 for taking multiple tissue samples. FIG. 8 is a side elevation view of the endoscopic biopsy device 2, and FIGS. 9 and 10 are side cross-sectional views in a cross-section along line IX-IX in FIG. 8 with the jaws in the OPEN position (FIG. 9) and in the CLOSED position (FIG. 10), respectively.

The endoscopic biopsy device of FIGS. 8-10 has three jaws 20, 21, 22 that are hinged to a distal end of a tubular body 10 by tongue-shaped flexible hinges 26, 27, 28. The jaws 20, 21, 22 are arranged in a three-fold symmetry around a central axis of the tubular body 10. The tubular body 10 has an internal cavity defining a collecting chamber 13 for collecting multiple tissue samples 10*x*, wherein the flexible hinges 26, 27, 28 are defined at the distal end thereof by longitudinal cuts in the peripheral wall of the tubular body 10. The flexible joints 26, 27, 28 are outwardly biased springs, wherein the relaxed state of these tongue-shaped springs determines the OPEN position of the jaws 20, 21, 22 as seen in FIGS. 8 and 9. An outer sleeve 60 can be slid in the distal direction over the flexible joints 26, 27, 28 so as to gradually constrain their outward bending against the bias, eventually bringing the jaws 20, 21, 22 to their CLOSED position as shown in FIG. 10.

The jaws 20, 21, 22 comprise respective retaining elements 40, 41, 42 that are formed as radially inward bent projections pointing towards the central axis. In the CLOSED position, the jaws 20, 21, 22 define a sampling chamber 23, which at its proximal end is delimited by the engaged retaining elements 40, 41, 42. The retaining elements 40, 41, 42 are shaped and dimensioned to define a partition between the sampling chamber 23 and a proximally adjacent collecting chamber 13 in the tubular body 10, thereby preventing the transfer of samples between the sampling chamber and the collecting chamber, yet leaving a central aperture 44 through which a collecting member 30 can be deployed.

For the purpose of holding collected tissue samples 10x, the endoscopic biopsy device 2 comprises the centrally arranged collecting member 30, that is oriented in the axial direction and that is provided with barbs 36 pointing in the proximal direction. The collecting member 30 is displaceable in the axial direction between a retracted position in the collecting chamber 13, and a deployed position, where the collecting member penetrates into a sampling chamber 23. In FIG. 9, the endoscopic biopsy device 2 is shown with the jaws 20, 21, 22 in the OPEN position, the retaining elements 40, 41, 42 disengaged, the collecting member 30 in a fully retracted position, and the endoscopic biopsy device 2 ready to grasp a tissue sample 100. FIG. 9 shows the endoscopic biopsy device 2 with the jaws 20, 21, 22 in the CLOSED position, and the retaining elements 40, 41, 42 engaged, wherein the collecting member carries a first tissue sample 100 transfixed thereon, and a further tissue sample 101 secured in the sampling chamber 23—ready to be transfixed by deploying the collecting member 30 through aperture 44.

Figure 11:
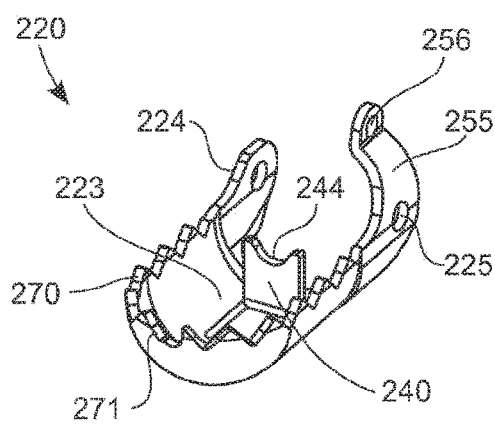
Figure 12:
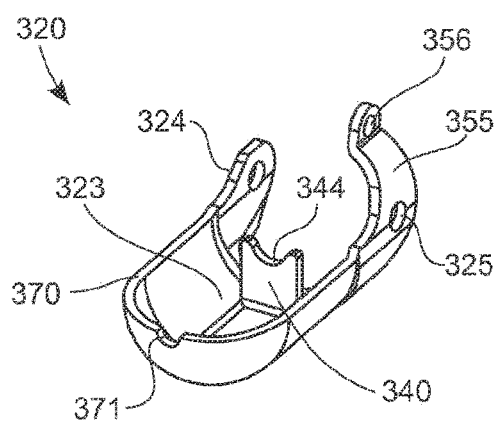

FIGS. 11 and 12 illustrate different profiles of cooperating jaw edges. FIG. 11 shows a jaw 220 defining a sampling chamber 223 in cooperation with a symmetric/complementarily shaped jaw (not shown). The jaw 220 has holes 224, 225 for receiving a pivot axis, and a lever 255 with an eyelet 256 for receiving an actuator, such as a rod for pull and push operation. A proximal end of the sampling chamber 223 is defined by a retaining element 240 in the form of a transverse wall with a recess 244 for allowing a collecting member (not shown) to pass when the retaining element is engaged. The jaw 220 has an edge 270, which cooperates with the complementary jaw to grip hold of a tissue sample. The edge 270 is provided with a serrated profile to improve gripping action. However, the edge 270 and the corresponding edge of the cooperating jaw are preferably made blunt, e.g. by beveling, chamfering or rounding the edges and features of the profile to avoid cutting through underlying tissue which should not be sampled and which should not be damaged.

FIG. 12 shows a jaw 320 defining a sampling chamber 323 in cooperation with a symmetric/complementarily shaped jaw (not shown). The jaw 320 has holes 324, 325 for receiving a pivot axis, and a lever 355 with an eyelet 356 for receiving an actuator, such as a rod for pull and push operation. A proximal end of the sampling chamber 323 is defined by a retaining element 340 in the form of a transverse wall with a recess 344 for allowing a collecting member (not shown) to pass when the retaining element is engaged. The jaw 320 has an edge 370, which cooperates with the complementary jaw to grip hold of a tissue sample. The edge 370 is provided with a smooth profile. However, the edge 370 and the corresponding edge of the cooperating jaw are preferably made blunt, e.g. by beveling, chamfering or rounding the edges and features of the profile to avoid cutting through underlying tissue which should not be sampled and which should not be damaged.

The edges and features of the jaw profile of the jaws 220, 320 and their cooperating counterparts are preferably made blunt by providing a chamfer, bevel or rounding of the edges/features of the profile with a characteristic dimension at the scale of the jaw edge 270, 370, such as at least 5%, alternatively at least 10%, alternatively at least 20% of the wall thickness of the jaws 220, 320. Thereby, the jaw edges 270, 370 are achieved that are dull at the scale of the wall thickness of the jaws. Jaws 220, 320 with such non-sharp edges, which may have a smooth, serrated, toothed or waved profile, allow for grasping and holding the tissue sample without the risk of damaging underlying tissue.

The invention claimed is:

1. Endoscopic biopsy device for collecting multiple tissue samples, wherein the endoscopic biopsy device comprises:
    a tubular body having in an axial direction a distal end and a proximal end;
    at least a first jaw member and a second jaw member attached to the distal end of the body, wherein the first and second jaw members are moveable with respect to each other between an OPEN position and a CLOSED position to secure a tissue sample, wherein the first and second jaw members in the CLOSED position define a sampling chamber;
    a collecting chamber for receiving multiple tissue samples, the collecting chamber being located within the body in a proximal direction adjacent to the sampling chamber; and
    an axially extending collecting member for transfixing secured tissue samples, the collecting member being axially displaceable between a retracted position in the collecting chamber and a deployed position where the collecting member penetrates into the sampling chamber,
    wherein the first jaw member includes a first retaining element arranged to project radially inward on a proximal portion of the first jaw member, and wherein the second jaw member includes a second retaining element arranged to project radially inward on a proximate portion of the second jaw member,
    wherein at least the first and second retaining elements engage to separate the sampling chamber and the collecting chamber from each other when at least the first and second jaw members are in the CLOSED position, and
    wherein at least the first and second retaining elements disengage to provide a passage for the transfer of transfixed tissue samples into and out of the collecting chamber when at least the first and second jaw members are in the OPEN position.

2. Endoscopic biopsy device according to claim 1, wherein the first and second retaining elements are formed as a transversely oriented partition.

3. Endoscopic biopsy device according to claim 1, wherein the first and second jaw members are hinged to the body by pivot-joints.

4. Endoscopic biopsy device according to claim 1, wherein the first and second jaw members are hinged to the body by axially extending tongue-shaped flexible joints.

5. Endoscopic biopsy device according to claim 1, wherein cooperating edges of the first and second jaw members are blunt.

6. Endoscopic biopsy device according to claim 1, wherein the first and second jaw members along their cooperating edges are provided with a serrated, toothed and/or waved profile.

7. Endoscopic biopsy device according to claim 1, wherein the collecting member is a needle, the needle tip pointing in a distal direction.

8. Endoscopic biopsy device according to claim 1, wherein the collecting member is detachably coupled to an axially sliding stem, the stem being arranged proximally with respect to the body.

9. Endoscopic biopsy device according to claim 1, wherein the collecting member comprises one or more of radially projecting protuberances, a barbed tip and a retro-serrate surface.

10. Endoscopic biopsy device according to claim 1, wherein the first and second jaw members are operated by traction wires.

11. Endoscopic biopsy instrument comprising an elongate flexible shaft, an endoscopic biopsy device according to claim 1, arranged at a distal end of the shaft, and operating controls arranged at a proximal end of the shaft, wherein a distal portion of the endoscopic biopsy instrument is configured for insertion into the instrument channel of an endoscope and wherein the operating controls are configured to communicate with the endoscopic biopsy device through the shaft to control operation of the endoscopic biopsy device.

12. Method for taking multiple tissue samples using an endoscopic biopsy instrument, the method comprising the steps of
 (a) advancing a distal portion of the endoscopic biopsy instrument through an instrument channel of an endoscope to a sampling site,
 (b) operating at least first and second jaw members each being located at a distal end of the endoscopic biopsy instrument to secure a tissue sample from the sampling site in a sampling chamber defined between the first and second jaw members in a CLOSED position,
 (c) engaging at least first and second retaining elements arranged at a proximal end of the sampling chamber, the first jaw member including the first retaining element and the second jaw member including the second retaining element,
 (d) deploying a collecting member in a distal direction through the first and second retaining elements, into the sampling chamber and through the tissue sample, thereby transfixing the tissue sample,
 (e) disengaging the first and second retaining elements so as to allow the transfixed tissue sample to pass between the first and second retaining elements, and
 (f) retracting the collecting member in the proximal direction, thereby transferring the transfixed tissue sample to a collecting chamber, the collecting chamber being arranged in a proximal direction adjacent to the sampling chamber.

13. Method according to claim 12, further comprising the steps of
 (g) moving the biopsy instrument to a further sampling site,
 (h) operating the first and second jaw members to secure a further tissue sample from the further sampling site in the sampling chamber,
 (i) engaging the first and second retaining elements,
 (j) deploying the collecting member in the distal direction through the engaged first and second retaining elements, into the sampling chamber and through the further tissue sample, thereby transfixing the further tissue sample while retaining already transfixed tissue samples in the collecting chamber by means of the first and second retaining elements acting against the displacement of the already transfixed tissue samples in the distal direction with the collecting member and shifting their position towards the proximal end of the collecting member,
 (k) disengaging the first and second retaining elements, and
 (l) transferring the newly transfixed further tissue sample to the collecting chamber by retracting the collecting member in the proximal direction.

14. Method according to claim 13, further comprising repeating steps (g)-(l) in order to collect one or more yet further tissue samples from one or more yet further sampling sites one by one.

15. Method according to claim 12, further comprising removing the endoscopic biopsy instruments from the endoscope to retrieve collected tissue samples.

16. Endoscopic biopsy device according to claim 2, wherein the first and second jaw members are hinged to the body by pivot-joints or by axially extending tongue-shaped flexible joints.

17. Endoscopic biopsy device according to claim 2, wherein the collecting member is detachably coupled to an axially sliding stem, the stem being arranged proximally with respect to the body.

18. Endoscopic biopsy device according to claim 1, further comprising at least a third jaw member also attached to the distal end of the body such that the first, second, and third jaw members are moveable with respect to each other between the OPEN position and the CLOSED position to secure the tissue sample,
 wherein the first, second, and third jaw members in the CLOSED position define the sampling chamber, the third jaw member including a third retaining element arranged to project radially inward on a proximate portion of the third jaw member.

19. Endoscopic biopsy device according to claim 18,
 wherein the first, second, and third retaining elements engage to separate the sampling chamber and the collecting chamber from each other in response to the first, second, and third jaw members being in the CLOSED position, and
 wherein the first, second, and third retaining elements disengage to provide a passage for the transfer of transfixed tissue samples into and out of the collecting chamber in response to the first, second, and third jaw members being in the OPEN position.

20. Method according to claim 12,
 wherein the operating includes operating a third jaw member located at the distal end of the endoscopic biopsy instrument to secure the tissue sample from the sampling chamber defined between the first, second, and third jaw members in the CLOSED position,
 wherein the engaging includes engaging a third retaining element arranged at the proximal end of the sampling chamber, the third jaw member including the third retaining element, wherein the deploying includes deploying the collecting member in the distal direction through the engaged first, second, and third retaining elements, and wherein the disengaging includes disengaging the first, second, and third retaining elements to allow the transfixed tissue sample to pass between the first, second, and third retaining elements.

\* \* \* \* \*